US012075997B2

(12) United States Patent
Parker

(10) Patent No.: US 12,075,997 B2
(45) Date of Patent: Sep. 3, 2024

(54) NON-INVASIVE TISSUE RETRACTOR

(71) Applicant: John Richard Parker, West Chester, PA (US)

(72) Inventor: John Richard Parker, West Chester, PA (US)

( * ) Notice: Subject to any disclaimer, the term of this patent is extended or adjusted under 35 U.S.C. 154(b) by 227 days.

(21) Appl. No.: 16/522,807

(22) Filed: Jul. 26, 2019

(65) Prior Publication Data

US 2021/0022721 A1   Jan. 28, 2021

(51) Int. Cl.
*A61B 17/02* (2006.01)
*A61B 17/08* (2006.01)
*A61B 17/00* (2006.01)

(52) U.S. Cl.
CPC .............. *A61B 17/02* (2013.01); *A61B 17/08* (2013.01); *A61B 2017/00544* (2013.01)

(58) Field of Classification Search
CPC .... A61B 2017/0225; A61B 2017/0443; A61B 17/08; A61B 2017/0287; A61B 17/02–0218
See application file for complete search history.

(56) References Cited

U.S. PATENT DOCUMENTS

| | | | | |
|---|---|---|---|---|
| 3,507,274 | A * | 4/1970 | Soichet | A61F 6/144 128/840 |
| 5,895,352 | A * | 4/1999 | Kleiner | A61B 17/02 600/209 |
| 8,721,629 | B2 * | 5/2014 | Hardman | A61B 17/085 604/543 |
| 8,986,326 | B2 * | 3/2015 | Satake | A61B 17/10 606/151 |
| 2005/0059985 | A1 * | 3/2005 | Kimura | A61B 17/083 606/151 |
| 2009/0030447 | A1 * | 1/2009 | Measamer | A61B 17/0218 606/205 |
| 2014/0364829 | A1 * | 12/2014 | Parker | A61M 3/0262 604/500 |
| 2017/0361012 | A1 * | 12/2017 | Parker | A61M 1/774 |
| 2021/0077086 | A1 * | 3/2021 | Tsubouchi | A61B 17/0293 |
| 2021/0236108 | A1 * | 8/2021 | Price | A61F 2/02 |

FOREIGN PATENT DOCUMENTS

BR    102019021460 A2 *   4/2021

* cited by examiner

*Primary Examiner* — Eduardo C Robert
*Assistant Examiner* — Steven J Cotroneo
(74) *Attorney, Agent, or Firm* — Laurence Weinberger

(57) ABSTRACT

A device for retracting or opening and closing a tissue wound employs two or more retractor arms that do not enter or penetrate into the wound or incision. The retractor arms engage the tissue on either side of the wound and apply outward or inward pressure on the tissue surface to open or close the wound.

19 Claims, 4 Drawing Sheets

Figure 3:
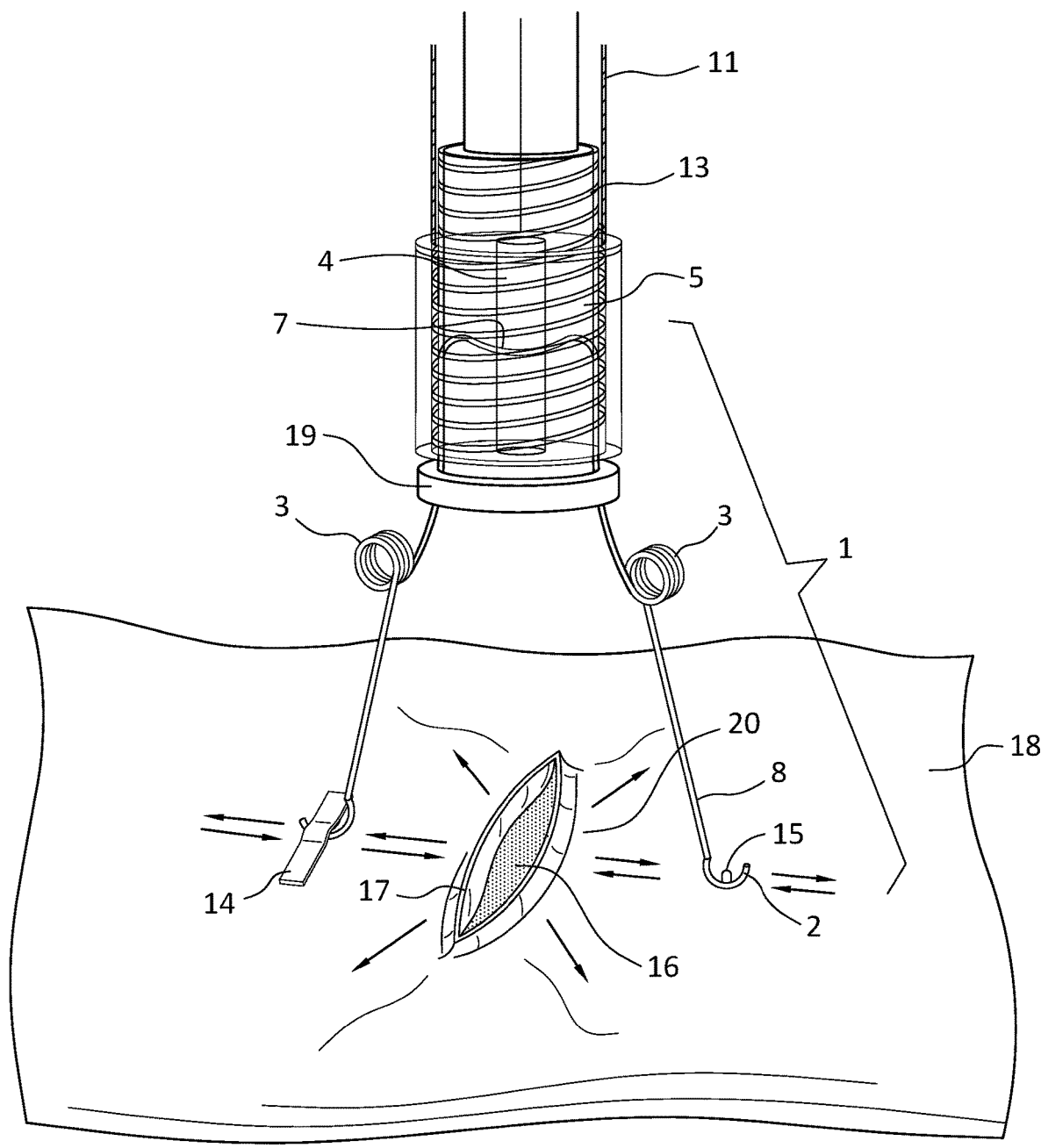

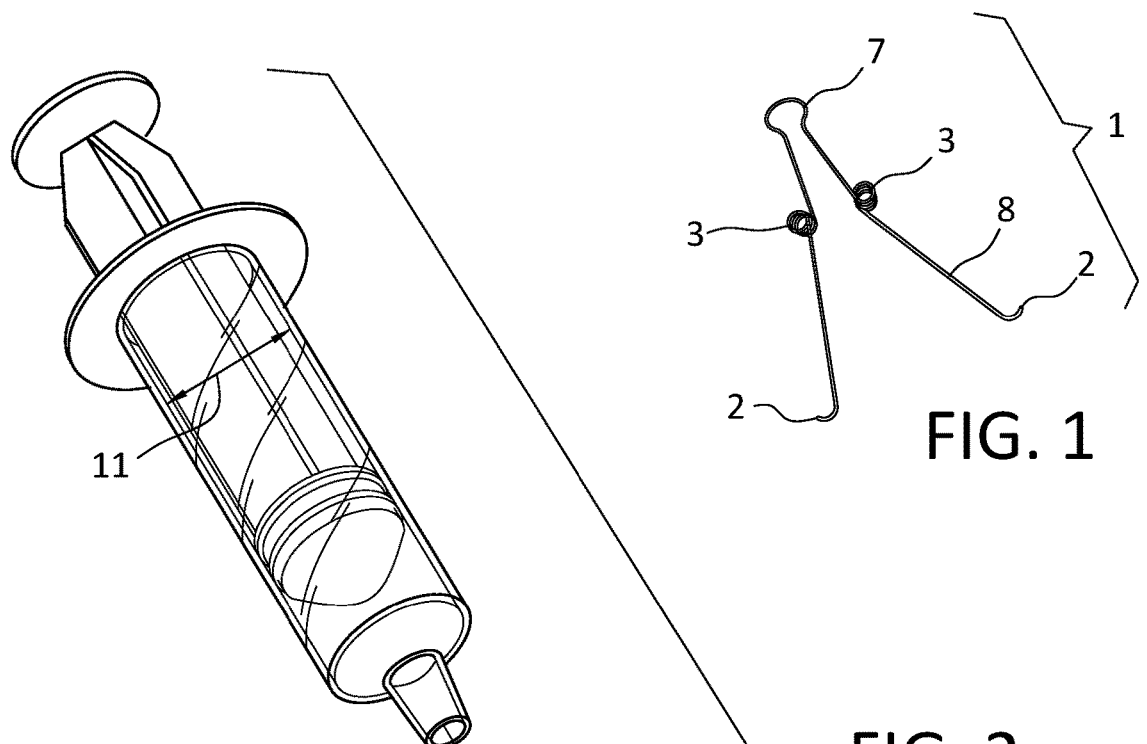
FIG. 1
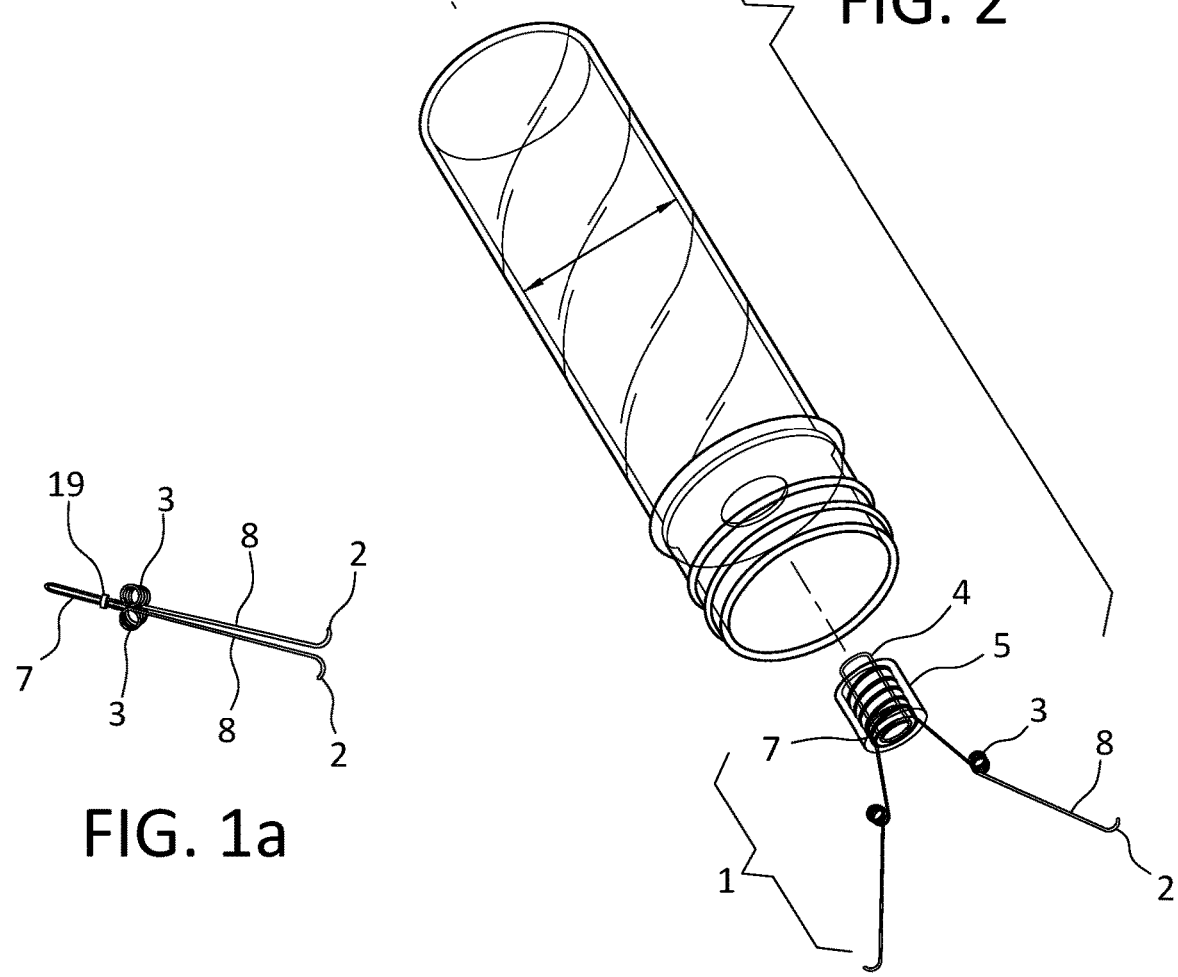
FIG. 1a
FIG. 2

NON-INVASIVE TISSUE RETRACTOR

1. BACKGROUND OF THE INVENTION

Field of the Invention

In the medical sector, there are many cases where wounds and incisions must be held open or closed for medical procedures and surgeries. Many times these wounds are small to medium in size, relatively shallow and in extremely difficult areas where there is very little room to retract the wound to perform the needed medical procedure. The I 2X is the only noninvasive retractor to be able to perform retraction or closing in extremely tight environments such as fingers between fingers, toes and between toes, ears, certain body cavities and openings and other hard to reach places. Many retractors look and perform almost identically but are specifically designed for unique and specific operation modality. The I 2X is designed for specific application that no other noninvasive retractor can perform due to its method of operation and overall size profile. No other retractor noninvasively retracts or holds the wound closed for gluing, suturing or other procedures where a wound or incision must be held open or closed without disengaging the retraction device. This new method is extremely critical to a multitude of medical procedures.

Description of the Problem and Prior Art

The devise described herein is an advancement over the retractor described in U.S. Pat. No. 9,981,081. Medical practitioners find it extremely difficult to retract and add or close the tissue of wounds and incisions in certain areas of close proximity and involving a variety of medical procedures. An example of this is hand surgery in the areas of the fingers, where it is very difficult to use the current methods of minimally invasive retraction due to fact that there is very little space to work in, plus the invasive nature of the retractor is in the way visually, causes trauma to the wound and makes wound retraction and the process difficult to impossible.

An approach is needed that employs a noninvasive, very low profile, retractor that can perform in extremely tight quarters without entering the wound. The I 2X is the only retractor that can noninvasively perform a prolifera of tasks in this specific and unique manner for very tight surgical environments.

2. BRIEF DESCRIPTION OF THE FIGURES

FIG. 1, FIG. 1a show a partially exploded view of the I 2X Retractor from the top (FIG. 1) and side view (FIG. 1a) with the retractor arm positioning sleeve (19) closing and retaining the wound closed (16, 17).

FIG. 2 shows the I 2X Retractor's interior upper partial loop-like bend screwed into the threads of a luer lock (5) on an Interceptor medical device. This is an example of the I 2X being used as an accessory to another medical device, using its interior upper partial loop-like bend end to engage a luer lock thread. In some cases, an I 2X would have a male luer lock thread as part of the upper partial loop-like bend at the interior end to engage the female component luer lock.

FIG. 3 shows the I 2X screwed into and engaged into a luer lock of a standard plunger type syringe (13, 11). In this view, the I 2X is being used to retract or close, by use of a retractor arm positioning sleeve, the wound noninvasively, making use of an adhesive surgical tape (14) as an anchoring device on the distal left-hand side and being anchored on the distal right-hand side by a pin (15) placed into the tissue surface (18).

ANOTHER EXAMPLE

Figure 4:
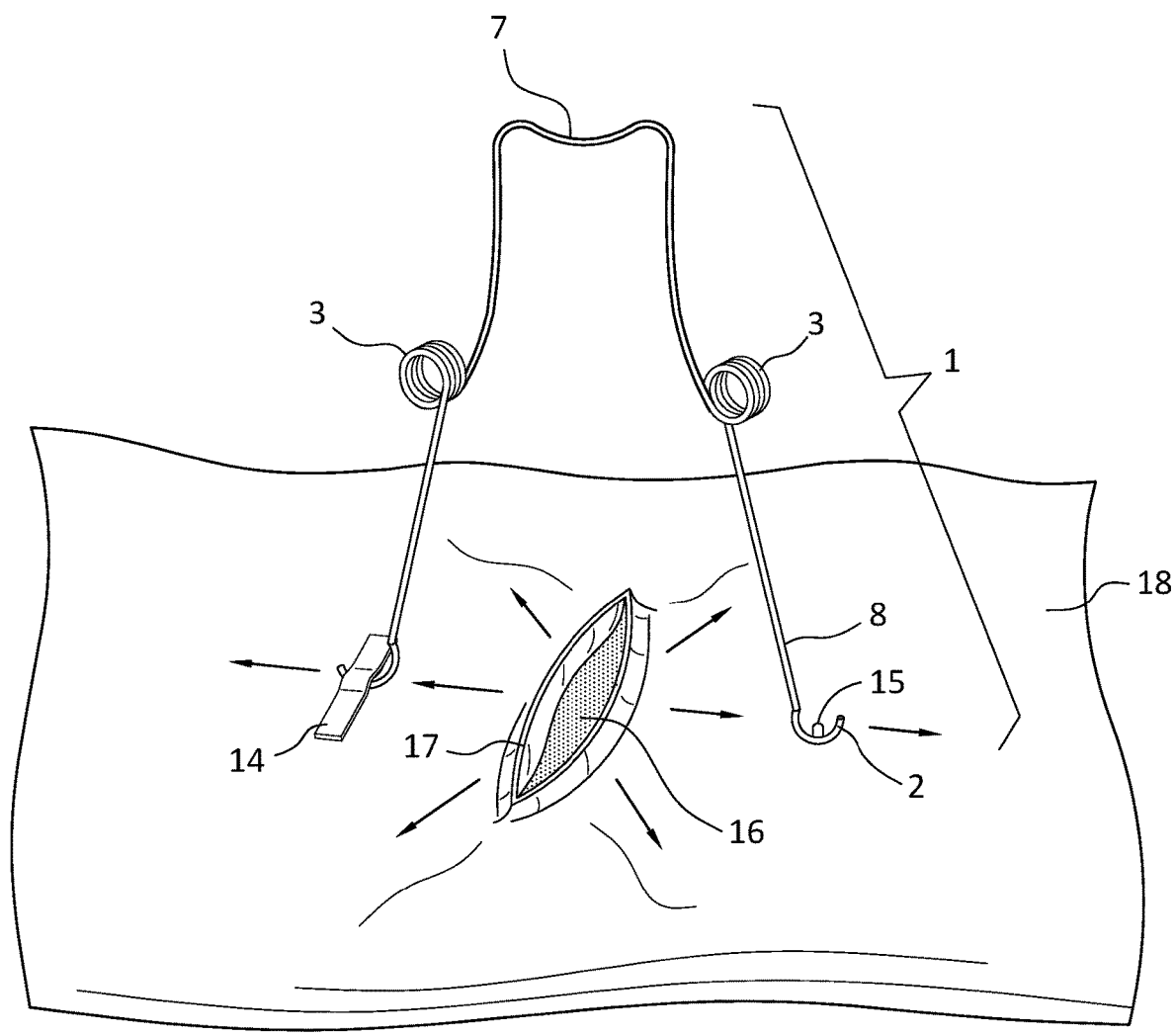

FIG. 4 shows the I 2X Retractor in a standalone, hands free open mode. In this view, the I 2X Retractor is not employed as an accessory to another device. The view in FIG. 4 depicts the Retractor making use of anchoring methods (tape 14, pin 15) to open or close (if the retractor arm positioning sleeve is added) and retain the position and topography of a wound in a confined operating environment in a unique noninvasive manner.

Figure 5:
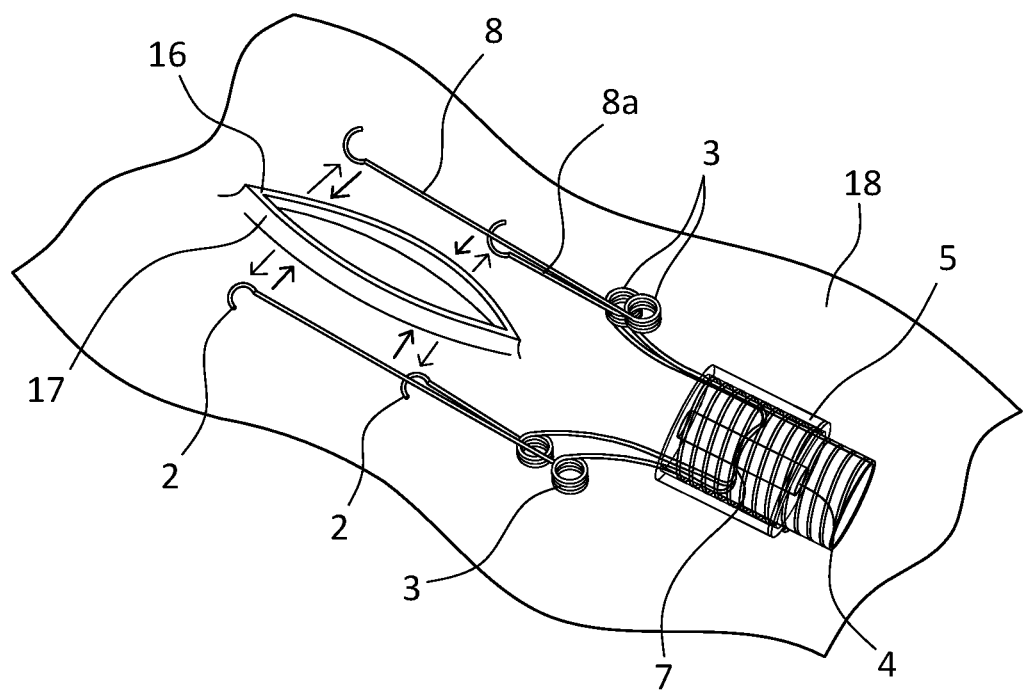

FIG. 5 shows the flexibility of the I 2X to make use of more than two retractor arms to perform specific retraction or closing methods. In this view, the I 2X is connected and screwed into a luer lock, which implies that it is being used as an accessory to another medical device, such as a syringe, an Interceptor or some other medical device employing the use of a luer lock to accommodate I 2X noninvasive retraction or wound closure.

Figure 6:
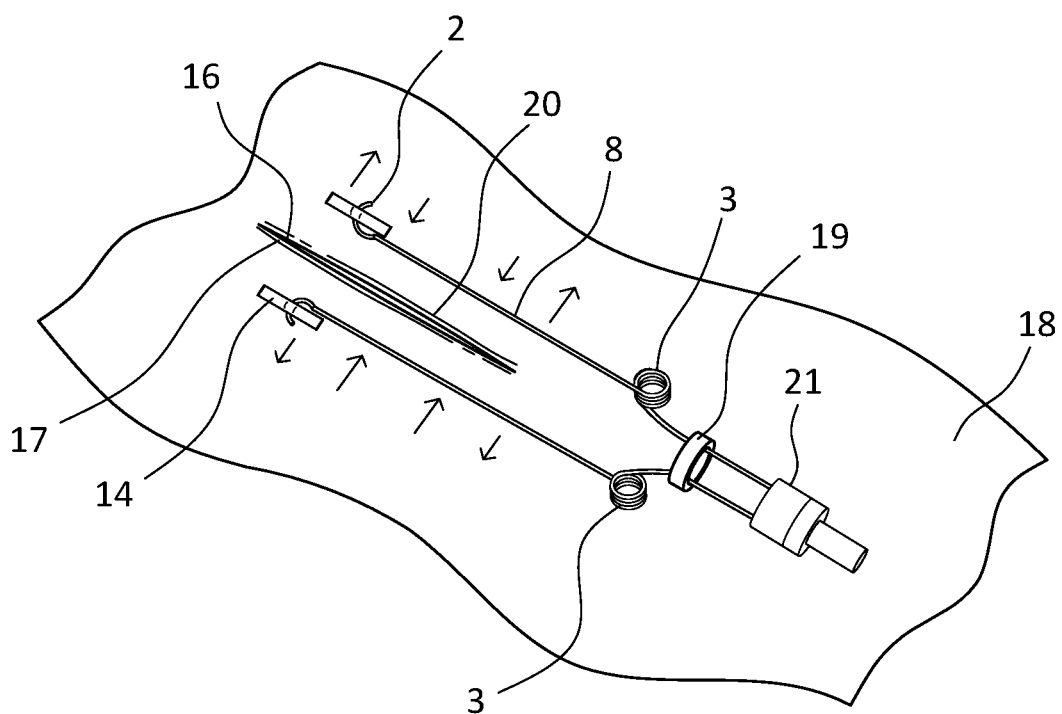

FIG. 6 shows the retractor arms (8) extended outward and the mechanism at the distal end (2) of the retractor arms engaging the tissue, which needs to be moved, retracted or repositioned in an inward or outward manner. The figure also depicts I 2X possessing a male luer lock as opposed to a loop-like bend at the anterior end of the retractor arms.

3. DETAILED DESCRIPTION OF THE INVENTION

Definitions

In the following description of the invention, DISTAL refers to the end of the device or its parts that will be closest to the site of the application against the skin during use. In the following description of the invention, ANTERIOR refers to the end of the device or its parts that will be furthest from the site of application against the skin during use.

Description

The present invention provides an I 2X device and method by which certain difficult to reach wounds may be accessed and noninvasively retracted or closed for medical surgery and procedures. The present invention provides a tissue retractor or closer (1) that may be used to open and hold open or close and retain closed small wounds or incisions. In the figures, like numbers denote the same parts. The I 2X (1) is, in part, comprised of a continual single strand of fabricated material wire like in nature and, in many cases, this single strand of fabricated material is medical grade stainless steel but not in every case. This single strand of spring like material undergoes a series of bends.

These bends serve a specific purpose, starting with the partial loop-like bend (7) at the anterior end of the device which is fabricated and pitched to accommodate the threads of a luer lock device, which is found to be employed by medical devices such as common syringes. The partial loop-like bend (7) at the anterior end of the device extends on both sides downward to make a retractor arm assembly (8). This retractor arm assembly (8) accommodates spring-like action with the inclination to spring or expand outward (or by use of its retractor arm positioning sleeve be limited to a more closed position) but with a spring-like propensity in an outward direction from its central location to pull a wound or incision in an outward or open manner (FIG. 3). Partway down the retractor arm (8) of the I 2X can be found an alternative coil, which in part is the continuation of the retractor arm itself in a coiled manner. This coil (3), if added to the device as an alternative, accommodates certain specific needs and creates a shift in vector and pitch to the action and motion of the retractor arm (8). At the furthest distal point of the I 2X is found a bend (2) in the retractor arm somewhat below the optional coil (3) to accommodate skin contact and friction or anchoring alternatives.

As the I 2X is applied to the wound area (16), the ends (2) of the retractor arms contact the skin (18) first and then spread outwards from wound (16), pulling the skin around the wound slightly taut, thereby tightening or retracting the skin away from the wound. In FIG. 5, a greater or lesser number of retractor arms (8, 8a) may be used. The important feature is that the retractor arms result in forming or positioning the wound opening to permit a more efficient operation and better accessibility because the device does not enter the wound or incision to hold it opened or closed. At the same time, this tightening in a direction away from the center of the wound allows for a puckering (17) at the edge of the wound (16), which allows for pooling of antiseptic for high concentration applications, for example. This retraction method is accomplished in a unique, low profile, noninvasive method. In an alternative embodiment, shown in FIG. 3, the retractor arms at the anterior end (7) has engaged a female luer lock thread, fastening itself to the distal end of a syringe. The female luer lock (5) engages the anterior end of I 2X by use of the bend (7) at the anterior end as I 2X engages and screws into the threads of said luer lock, which is in part the distal end of the syringe (11) containing the piston plunger (13) and nozzle (4). This embodiment (FIG. 3) is yet another example of the Retractor I 2X being used as an accessory to a medical device. Under the above circumstances, this method may be used to maintain a wound open for irrigation and flushing of debris or pathogens, internal application of epinephrine or lidocaine, manual removal of debris from a wound, surgical application requiring alternate medication drips administered to the wound.

The device may be unscrewed and disengaged from the medical device it was used with as an accessory and then become a hands free, standalone retractor with extremely low profile and noninvasive attributes for specific applications, noted in FIG. 4. As seen in the embodiment in FIG. 1, FIG. 1A and FIG. 5, the I 2X Spreader Retractor utilizes two or more retractor arms (8) substantially located 180 degrees apart on opposite sides. It is important that the retractor arms be located opposite each other to work against each other to retract the wound or incision equally from both sides of the wound (16). In addition to the restoring action of the optional coils (3), the material from which the long retractor arms are made of also provides additional resilience to the displacement. Retractor arms (8) made with material with greater resistance to displacement may be employed, depending on the spreading force requirement for particular wound, incisions and methodology. Typically, the retractor arms are formed from stainless steel, which may be disinfected or sterilized so that the Retractor may be used in a variety of medical settings to sustain long-term opening or closing of a wound or incision.

The retractor arms (8) may be anchored to the tissue surface (18) by means of, but not limited to, adhesive strips, pins, adhesives, and, but not limited to, medical grade glues and fastening devices. The ends/contact surfaces (2) of retractor arms (8) may be adapted to particular anchoring methods, as will be well understood by those skilled in the art. For example, a longer end (2) of retractor arms (8) may be provided for use with adhesive anchoring strips (14) as shown in FIG. 3. Alternatively, an end (2) of retractor arm (8) with a slight hook may be provided to engage a pin (15) as shown in FIG. 3 and FIG. 4. Where appropriate, the anchoring means may be applied to the tissue surface before the retractor arms (8) are engaged. As a further example, the ends/contact surfaces (2) of the retractor arms may be coated with a soft adhesive so that, as they engage the tissue surface, the ends/contact surfaces (2) of the retractor arms are anchored to the tissue surface.

In order to use the wound retractor of this application, the longer retractor arms (8) may be pinched together or inwardly by the user, and, after engaging one of the anchoring means, released. The combined resilience of the material of which retractor arms (8) are made in addition to the resilience and vector distribution of the alternative coils (3) provides an outward thrust, thereby opening the wound or incision (16) to the appropriate shape for the intended procedure. Not only do the coils (3) provide additional outward thrust to the retractor arms (8), but they also provide for a change of pitch of the retractor arm (8), providing an outward component away from the plane of the tissue surface (18) to achieve the desired wound topography. Anchored in this manner, the outward thrust of the retractor arms, indicated by the arrows on the tissue surface in FIG. 3 and FIG. 4, increases as the retractor arm assembly (1) is moved toward the tissue surface (18), increasing the pressure applied by the retractor arm retractor (1). Under most circumstances, the optional coils (3) in the retractor arms (8) are essential to enabling the retractor arm ends/contact surfaces (2) to move downward and outward in the desired manner by maintaining outward thrust even as more pressure is exerted by the decreasing distance of the retractor arm retractor (1). It is to be noted that the only time the device (1) is chosen that does not contain the optional coils (3) or optional retractor arm positioning sleeve (19) is when the space or circumstances in which the I 2X is operating do not allow for the additional area, which is taken up by the coils (3) and, in some cases also, the optional retractor arm positioning sleeve.

Utilized in this manner, the retractor arms (8) position the wound or incision (16) in a specific topography and shape. Unlike prior art retractors, which are larger and must be invasively inserted into a wound, the retractor arm (8) of this embodiment do not intrude into the wound or incision (16). The retractor arm does not just tighten the skin/tissue surface (18) on either side of the wound or incision but, most importantly, also opens the wound or incision (16) and puckers its shape (17). The outward thrust of the retractor arms (8) causes the wound to take on a specific puckered shape by rotating both tops of the wound or incision walls (17) away from the center of the wound or incision, thereby exposing the base of the wound and more surface area for more thorough access. A topography is developed in which the tops of the wound or incision walls rise above the surrounding tissue surface (18), thereby permitting debris and pathogens to flow away from the wound base during the flushing and irrigation process. Puckering also raises the base of the wound, which is important for complete flushing and removal of contamination. In many cases, puckering can cause pooling of antiseptics, which can increase concentration if allowed to remain for a given exposure interval. The above process, along with many different surgical and medical procedures, is accomplished without the retractor arms engaging the inside of the wound, which is a unique noninvasive process compared with prior art retractors. This unique noninvasive methodology allows for greater access, less wound trauma and an operational mode which lends itself to being able to perform in tight quarters noninvasively where other retractors cannot. Those skilled in the art will appreciate that various modifications and alterations may be made to the device and method described in this patent document, and such are considered to fall within the scope of this disclosure and appended claims.

COMPONENTS AND DESCRIPTIONS OF INTERCEPTOR 2X (I 2X)

1. A device for retracting, opening and closing a tissue wound or incision (I 2X)
2. The distal end, foot or hook of the Retractor I 2X
3. The coil located part way down from the anterior upper end of I 2X
4. The nozzle associated with a device such as a syringe, for example
5. The outer flange of a nozzle and luer lock assembly
6. Not used.
7. The anterior looped end of the I 2X used to engage the threads of a luer lock
8. The arms of the I 2X Retractor
   a. A Retractor I 2X with multiple retractor arms
9. Not used.
10. Not used.
11. The walls of a syringe housing
12. Not used.
13. A syringe piston or plunger
14. An anchoring device and method
15. An anchoring pin
16. A tissue wound or incision
17. A wound wall section
18. Tissue or skin
19. The retractor arm positioning sleeve for wound positioning
20. A positioned wound
21. A male luer lock component fixed stationary and part of the anterior end of I 2X as an alternative to the anterior loop

The invention claimed is:

1. A noninvasive retractor apparatus for closing or opening wounds and incisions, which occur in animal and human tissue, comprising
   a. a threaded luer lock;
   b. a single strand of spring like wire material;
   c. a centrally located and pitched partial loop-like bend in the strand engaging the threads of the luer lock; and
   d. two arms extending downward from either side of the bend that converge but do not cross to define a gap between the ends of the arms.

2. The noninvasive retractor of claim 1 further comprising means at the ends of each retractor arm for anchoring the retractor arm to a tissue surface, wherein the retractor arms are configured to flexibly apply pressure to the tissue surface to close or open the wound in the tissue in the immediate area of the wound in a direction outward or inward toward the wound center.

3. The noninvasive retractor of claim 1 further comprising spring coils located approximately about half the length of each retractor arm.

4. The noninvasive retractor of claim 1 further comprising means at the ends of each retractor arm for anchoring the retractor arms to a tissue surface.

5. The noninvasive retractor of claim 4 in which the means at the ends of each retractor arm for anchoring the retractor arms comprises an adhesive or non-slip material.

6. The noninvasive retractor of claim 4 in which the means at the ends of each retractor arm for anchoring comprises mechanical attachment.

7. The noninvasive retractor apparatus of claim 1 further comprising a repositionable positioning sleeve encircling the retractor arms as a means for causing the distance between the retractor arms to vary.

8. A noninvasive retractor apparatus for closing or opening wounds and incisions, which occur in animal and human tissue, having two pairs of flexible retractor arms each pair comprising:
   a. a threaded luer lock;
   a. two strands of spring like wire material;
   b. a centrally located and pitched partial loop-like bend in each strand engaging the threads of the luer lock; and
   c. two (retractor) arms extending downward from either side of the bend on each strand that converge but do not cross to define a gap between the (ends of the) arms.

9. The noninvasive retractor apparatus of claim 8 further comprising spring coils located approximately about half the length of each retractor arm.

10. The noninvasive retractor of claim 9 further comprising means at the ends of each retractor arm for anchoring the retractor to a tissue surface.

11. The noninvasive retractor of claim 10 in which the means at the ends of each retractor arm for anchoring the retractor arms comprises an adhesive or non-slip material.

12. The noninvasive retractor of claim 10 in which the means at the ends of each retractor arm for anchoring the retractor arm comprises mechanical attachment.

13. The noninvasive retractor of claim 8 in which the retractor arms of one pair are longer than the retractor arms of the other pair.

14. The noninvasive retractor of claim 13 in which spring coils are located approximately about half the length of each retractor arm.

15. The noninvasive retractor of claim 13 further comprising means at the end of each retractor arm for anchoring the retractor arms to a tissue surface.

16. The noninvasive retractor of claim 15 in which the means at the end of each retractor arm for anchoring the retractor arm comprises an adhesive or non-slip material.

17. The noninvasive retractor of claim 15 in which means at the ends of each retractor arm for anchoring the retractor arm comprises mechanical attachment.

18. A method of noninvasively opening or closing a tissue wound or incision using the noninvasive retractor of claim 13, comprises placing the retractor substantially parallel to the tissue surface with the shorter retractor arms of each pair placed near the end of the wound or incision closest to the anterior end of the retractor arms and the longer retractor arms placed further away.

19. The noninvasive retractor apparatus of claim 8 further comprising a repositionable positioning sleeve encircling each pair of the retractor arms as a means for causing the distance between the retractor arms to vary.

* * * * *